United States Patent [19]

Römhild et al.

[11] Patent Number: 4,820,153
[45] Date of Patent: Apr. 11, 1989

[54] PROCESS AND APPARATUS FOR CLEANING A TOOTH

[75] Inventors: Ludwig Römhild, Am Kugelfeld 3, Berchtesgaden, Fed. Rep. of Germany; Erwin Hartmann, Möriken; Peter Reinhard, Weingartenstrasse 8, Spreitenbach, both of Switzerland

[73] Assignees: Ludwig Römhild, Berchtesgaden, Fed. Rep. of Germany; Peter Reinhard, Spreitenbach, Switzerland

[21] Appl. No.: 927,008

[22] Filed: Nov. 4, 1986

[30] Foreign Application Priority Data

Nov. 6, 1985 [CH] Switzerland ............... 4763/85
Sep. 15, 1986 [CH] Switzerland ............... 3691/86

[51] Int. Cl.$^4$ ................................ A61C 1/07
[52] U.S. Cl. ................................ 433/118; 433/122; 433/143
[58] Field of Search ............ 433/118, 122, 143, 119, 433/120, 123

[56] References Cited

U.S. PATENT DOCUMENTS 1,046,560 12/1912 Coulson .................... 433/143
2,751,685 6/1956 Sharon et al. .............. 433/122
4,341,519 7/1982 Kuhn et al. ................ 433/122

FOREIGN PATENT DOCUMENTS 0413686 5/1925 Fed. Rep. of Germany ...... 433/122
0650678 9/1937 Fed. Rep. of Germany ...... 433/122

Primary Examiner—Gene Mancene
Assistant Examiner—Adriene J. Lepiane
Attorney, Agent, or Firm—Helfgott & Karas

[57] ABSTRACT

A process for treating periodontitis existing in the mouth of a patient having teeth with roots extending downwardly in the gums by using a scaler including a scraper with a cutting edge and a handle for the scraper. A dentist uses the scraper to remove tartar, concretions and necrotic root element from a tooth by guiding the cutting edge along the tooth root under the gums from the lowest point of the gum pocket and while exerting pressure on the root suddenly moving the cutting edge with a powerful jerk in scraping manner toward the chewing face of the tooth. The scaler is adapted for manual movement by the dentist and also has a mechanism which when actuated initiates and performs the jerk action without manual movement of the scraper by the dentist.

13 Claims, 4 Drawing Sheets

PROCESS AND APPARATUS FOR CLEANING A TOOTH

BACKGROUND OF THE INVENTION

In the treatment of periodontitis, it is known to use hand-operated instruments, known as scalers for cleaning the tartar, concretions (the particularly hard subgingival tartar) and necrotic root element from the tooth. The dentist holds the scaler in much the same way as a writing instrument between the thumb, index finger and middle finger. The scaler is essentially a scraper provided with a handler. The scraper carries a scraping insert, with the cutting edge of which the tooth is cleaned. The middle finger is supported on the "shovel" face of the tooth and the cutting edge of the scraper insert is guided along the tooth root under the gums and from the lowest point of the gum pocket and whilst exerting pressure on the tooth root is suddenly moved with a powerful jerk in scraping manner towards the chewing face of the tooth. This process is repeated until the deposits are removed.

Each movement must be performed with a great amount of effort and very precisely, in order to avoid injury. A further problem is that the movement sequence to be performed by the dentist must be carried out with an unfavourable force application, so that the hand rapidly becomes fatigued. Therefore this constitutes one of the hardest manual activities of the dentist.

SUMMARY OF THE INVENTION

An object of the present invention is to provide a new process for treating periodontitis wherein a dentist can manually remove tartar, concretion and necrotic root element with much less effort than previously required.

Another object is to provide a new type of scaler for use by a dentist in treating periodontitis wherein the manual efforts of the dentist are minimized.

More particularly, the process is adapted for treating periodontitis existing in the mouth of a patient having teeth with roots extending downwardly in the gums by using a scaler including a scraper with a cutting edge and a handle for the scraper. A dentist uses the scraper to remove tartar, concretions and necrotic root element from a tooth by guiding the cutting edge along the tooth root under the gums from the lowest point of the gum pocket and while exerting pressure on the root suddenly moves the cutting edge with a powerful jerk in scraping manner toward the chewing face of the tooth. The scaler is adapted for manual movement by the dentist and also has means which when actuated initiates and performs the jerk action without manual movement of the scraper by the dentist, the process includes the steps of manually moving the edge by manual operation of the dentist until the jerk action is desired and then automatically initiating and performing said action without movement of the scaler by the dentist.

The scaler for use in the treatment of periodontitis employs an elongated striking rod having a bore in one end; and an elongated handle. The scraper is disposed in the handle and is longitudinally movable back and forth along the direction of elongation within the handle, the bore containing end of the rod extending out of the handle. The rod is connected to a scraper having a projecting end with a cutting edge, the scraper having an opposite end disposed in said bore. The scaler can include means in the handle for periodically initiating an action at which the rod is first moved rapidly outward with respect to the handle and almost immediately thereafter is moved rapidly inward to be returned to the original position in the handle.

The aforementioned objects and advantages of the invention as well as other objects and advantages thereof will either be explained or will become apparent to those skilled in the art when this specification is read in conjunction with the accompanying drawings and specific description of preferred embodiments which follow.

DESCRIPTION OF THE PREFERRED EMBODIMENTS

Figure 1:
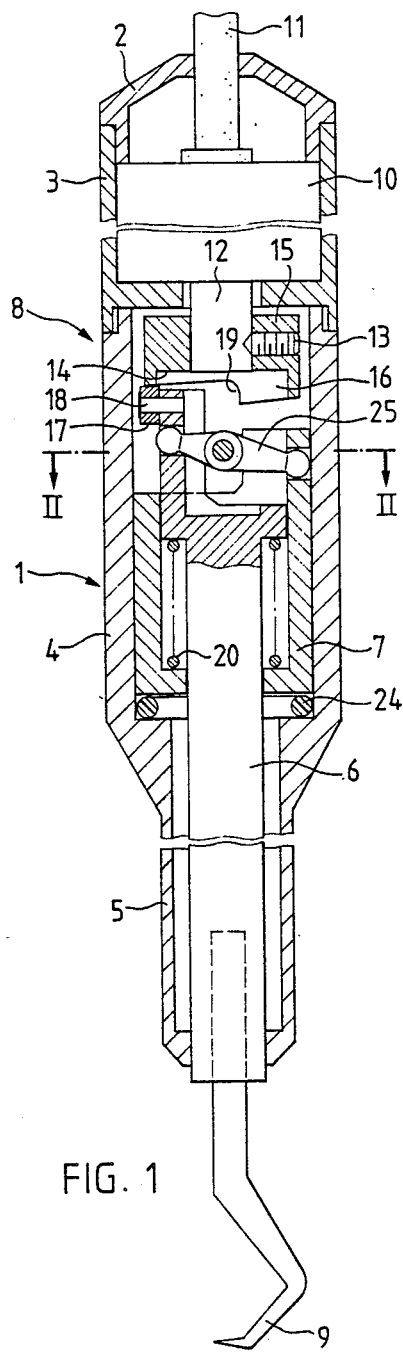
FIG. 1 is a longitudinal section through a scaler in accordance with one embodiment of the invention.

Referring now to FIG. 1 a hollow handle is provided with a cover 2, a rear casing 3 and a front casing 4. A casing neck 5 is connected to the front case 4. The rear casing 3 receives a drive means 10. Front 4 and casing neck 5 contains a striking rod 6, striking body 7 and transmission means 8. The transmission means 8 are differently constructed in the scalers according to FIGS. 1 to 8, but have the function of converting the movement of drive means 10 into a movement of striking rod 6. At its end remote from transmission means 8, striking rod 6 carries a scraper 9, which is used for cleaning a tooth. However, to enable said cleaning to be carried out, the scraper 9 must be moved relatively slowly away from the handle, whilst the return movement towards the handle must take place in a sudden and jerky manner.

In FIG. 1 the transmission means 8 comprises a link disk 15 and a feeler roll 17 mounted in rotary manner on striking rod 6 by means of a pin 18. The drive means 10 is an electric drive motor provided with an electrical connection 11 passing through cover 2 and which is optionally equipped with a reduction gear. A link disk 15 is mounted in fixed manner by means of a threaded pin 13 on the drive shaft 12 of the motor or gear and from the front face 14 thereof rises a link 16 constructed as a circular rim or edge. Link 16 forms a constantly sloping path on which the feeler roll 17 rolls and which at one point has a sudden transition 19. If, viewed from scraper 9, the link disk 15 rotates counterclockwise, the striking rod 6 is moved slowly away from the handle by feeler roll 17 and counter to the action of a working spring 20. At the sudden transition 19, striking rod 6 and therefore scraper 9 is moved in a sudden or jerky movement about the jump height of transition 19 in the direction of drive means 10. This movement corresponds to the manual striking movement which the dentist has to perform with a known scaler. In the scaler described in FIG. 1 this sudden or jerky movement is now automatically performed by the apparatus, so that the dentist is relieved of this strenuous activity.

The mass of the striking rod 6 moved in sudden manner will produce a reaction on handle 1, through which the handle is moved in the opposite direction and therefore substantially reduces the sudden return movement of scraper 9. To overcome this disadvantage, in the front casing 4 the striking body 7 is so coupled by means of a two-arm coupling level 25 to the striking rod 6, that striking body 7 performs a movement in the opposite direction to that of striking rod 6. As a result, during the sudden return movement of striking rod 6, the striking body ensures a mass equilibrium, so that during the return movement of scraper 9, handle 1 is immovable in the operator's hand. Working spring 20 assists the movement of striking rod 6 and striking body 7. An insert ring 24, e.g. made from an elastomer or some other plastics material, damps the movement of striking body 7 at the end of the return movement of scraper 9. The embodiments according to FIGS. 3 to 12 show scaler drives, all of which utilize a striking body 7 for mass compensation purposes. The only differences relate to the arrangement of striking rod 6, striking body 7 and the transmission means.

Figure 2:
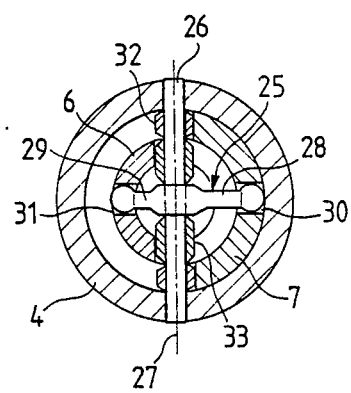
FIG. 2 is cross-section taken along line II of FIG. 1.

FIG. 2 shows the mounting of coupling lever 25, which is rotatably mounted on a shaft 26 with a pivot 27 and has a first arm 28 for driving striking body 7 and a second arm 29 for driving striking rod 6. The two arms 28, 29 extend into recesses 30, 31 in striking body 7 or striking rod 6. The arrangement of working spring 20 in FIGS. 1, 3 to 5, 7, 10 and 11 has the advantage that the drives of striking rod 6 or striking body 7 are kept free from play. The mass equilibrium thereof is not impaired even in the case of wear.

In view of the fact that the scrape must exert forces in specific directions, it is necessary to ensure that neither striking rod 6 nor striking body 7 rotate. Thus, according to FIG. 2, rollers 32, 33 are rotatably mounted on shaft 26. Striking body 7 is supported on rollers 32 and striking rod 6 on rollers 33.

In FIGS. 1 and 2 the two arms 28, 29 of coupling lever 25 have unequal lengths, but they can be equally long or have a different length ratio.

In FIGS. 3 to 8 the same reference numerals designate the same part as in FIGS. 1-2.

Figure 3:
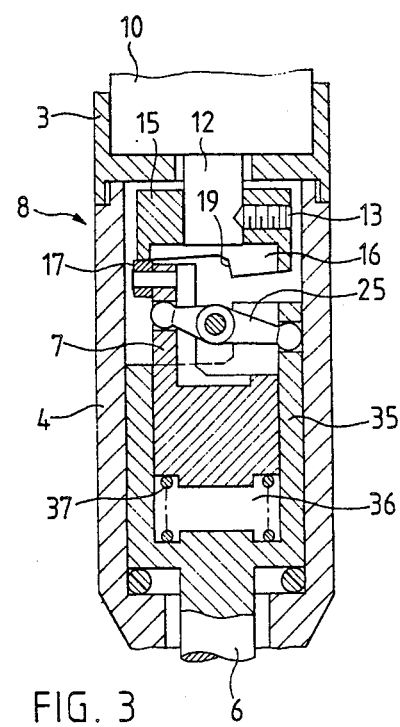
FIGS. 3-9 are views similar to FIG. 1 wherein different detailed arrangements of parts are illustrated.

In the embodiment according to FIG. 3, the scaler has the same transmission means 8, i.e. link disk 15, link 16 and feeler roll 17, as in the case of the embodiment of FIGS. 1 and 2. The difference is that feeler roll 17 is mounted in rotary manner on striking body 7. Striking body 7 is located in the interior of a sleeve-like attachment 35 of striking rod 6. A return spring 37 is placed in the cavity 36 between the end face of striking body 7 and the base of attachment 35.

In the embodiment according to FIG. 3 and when viewed from the scraper, link disk 15 rotates clockwise. On the constantly sloping edge of link 16, striking body 7 moves in the direction of drive means 10 and striking rod 6 in the opposite direction via coupling lever 25. For performing the sudden return movement of striking rod 6, the feeler roll 17 moves suddenly from the base of the sudden transition 19 on to the link rim or edge which is higher by the height of the jump, so that the striking rod 6 is retracted in a sudden or jerky manner. The return spring 37 merely serves to hold the feeler roll 17 on link 16. As in FIG. 1, drive means 10 is a motor, optionally with a reduction gear, whose drive shaft 12 performs a rotary movement. The electric motor of FIGS. 1 and 3 can be replaced by a hydraulic or pneumatic motor.

Figure 4:
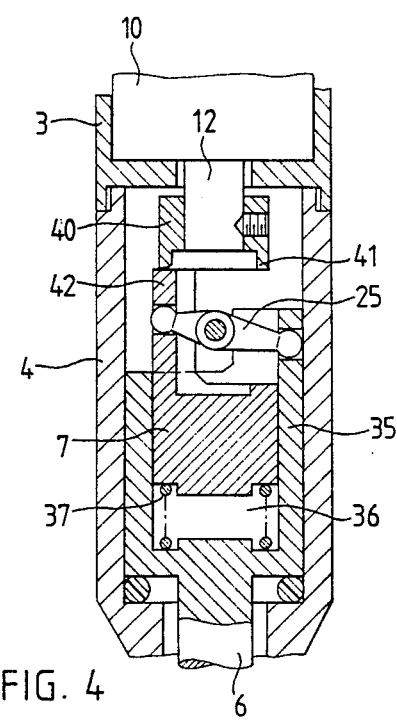

In the scaler embodiment according to FIG. 4, a lifting unit is used and its drive shaft 12 performs a reciprocating movement. A striking ring 40 is secured to the drive shaft 12. The front edge of ring 40 acts on an edge portion 42 of the striking body 7. As in the embodiment according to FIG. 3, striking body 7 is located in the interior of a sleeve-like attachment 35 of striking rod 6. Whenever edge 41 of striking ring 40 meets the edge portion 42 of striking body 7, there is a movement of the latter away from drive means 10 and simultaneously a return movement of striking rod 6. It is also possible in this way to obtain a sudden return movement of the scraper.

In FIG. 4 return spring 37 is also inserted in cavity 36. If this spring is removed, the function of the scaler is not impaired. In this case the operator assumes responsibility for the slow movement of scraper 9 away from the tooth contact surface in the direction of the tooth root. Striking rod 6 and therefore also the sleeve-like attachment 35 is moved in the direction of drive means 10, so that by means of coupling lever 25 edge portion 42 of striking body 7 is raised from edge 41 of striking ring 40. If handle 1 is now moved in the direction of the tooth root against the chewing face of the tooth, the scraper remains on the tooth contact surface, the striking rod 6 moves away from drive means 10 and striking body 7 towards said drive means until the edge 41 of the striking ring meets the edge portion 42, so that the sudden return movement of scraper 9 takes place. Here again, the scaler according to FIG. 4 automatically carries out the scraper return movement, which requires a considerable effort. The return movement can also take place in the form of a sequence of small return movements and then optionally a manual return movement is superimposed thereon.

Figure 5:
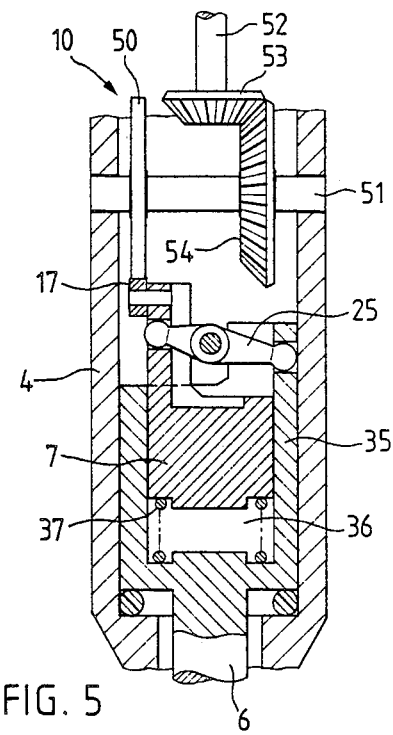

The embodiment of the scaler according to FIG. 5 is the same arrangement of the striking rod 6, striking body 7 and coupling lever 25 as in FIG. 3. The feeler roll 17 is mounted in rotary manner on striking body 7 as in FIG. 3. In place of link disk 15 a disk cam 50 is used on FIG. 5 and is fixed to a shaft 51. On the entire circumference of disk cam 50 is provided a constantly changing radius with a sudden transition (not shown). In the same was as in FIG. 3, said transition gives the striking body 7 a sudden movement away from drive means 10, which brings about a corresponding sudden return movement of striking rod 6.

In the construction according to FIG. 5, the drive means 10 is constituted by a motor performing a rotary movement, whose drive shaft 52 rotates shaft 51 and therefore the crank gear 50 by means of a bevel gear train with a pinion 53 and a bevel gear 54.

Figure 6:
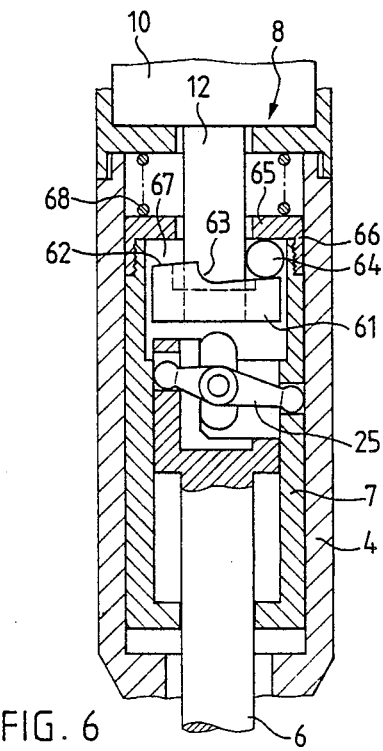

In the scaler embodiment according to FIG. 6 the drive means 10 rotates by means of drive shaft 12 a link disk 61, whose link 62 with the transition 63 is directed against drive means 10. A feeler ball 64 rolls freely on link 62 and is located in freely movable manner in the free space 67 formed by link 62 and flange 65 of a screw cover 66 screwed on to the striking body 7.

The rotary movement of link disk 61 takes place counterclockwise and when feeler ball 62 drops at the sudden transition 63 a working spring 68 moves the striking body 7 away from drive means 10, so that the striking rod 6 forms the sudden return movement with scraper 9.

Figure 7:
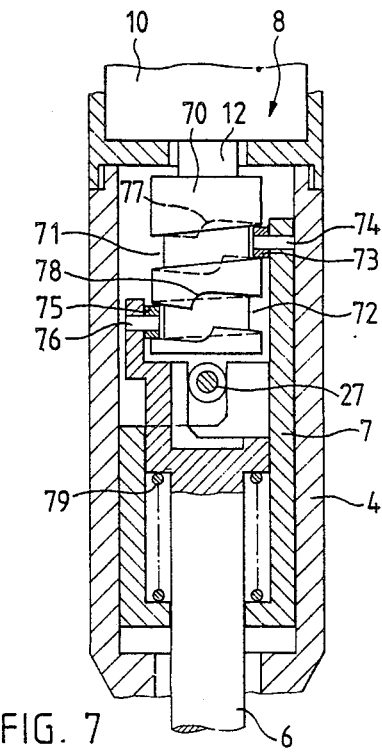
Figure 8:
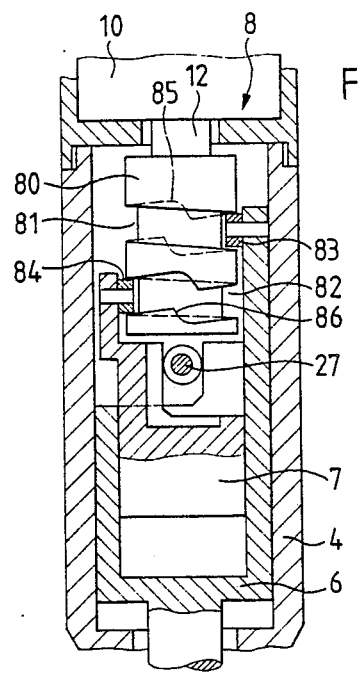

In the scaler embodiment according to FIGS. 7 and 8 striking rod 6 and striking body 7 are not coupled to a coupling lever as in the previously described embodiments. In FIG. 7 a link body 70 is mounted in fixed manner on drive shaft 12 of drive means 10 and has two link slots 71, 72 extending over the circumference, the link slot 71 closer to drive means 10 receiving a feeler roll 73, which is rotatably mounted on striking body 7 by means of a pin 74. In the link slot 72 more remote from drive means 10 is guided a feeler roll 75, which is mounted in rotary manner with a pin 76 on striking rod 6. The shape of link slots 71, 72 is such that at the sudden transition 77 of slot 71 striking body 7 is moved suddenly away from the drive means and striking rod 6 in an oppositely directly transition 78 of slot 72 is suddenly moved towards drive means 10. A working spring 79 aids the sudden movements of striking body 7 and striking rod 6.

In the scaler embodiment according to FIG. 8 a link body 80 is also fixed to the drive shaft 12 of drive means 10 and has two link slots 81, 82. A feeler roll 83 mounted in rotary manner on striking rod 6 is supported in slot 81 and a feeler roll 84 mounted in rotary manner on striking body 7 is supported in slot 82. In this embodiment the sudden transitions 85 of slot 81 and 86 of slot 82 are constructed in such a way that at these points the striking rod 6 performs a sudden movement towards drive means 10 and striking body 7 a movement away from said drive means. In the embodiments according to FIGS. 7 and 8 the rotary movement of drive shaft 10 takes place clockwise, viewed from scraper 9. In both embodiments there are also means for preventing a rotary movement of striking rod 6 and striking body 7 in the form of a shaft 27 (cf. FIG. 2), which is mounted in the front casing part 4 and carries the rotary rolls, on which are supported striking rod 6 and striking body 7.

In the embodiment according to FIG. 8 there is no working spring as in FIG. 7. The sudden movements are in this case solely ensured by the sudden transitions 85, 86.

Figure 9:
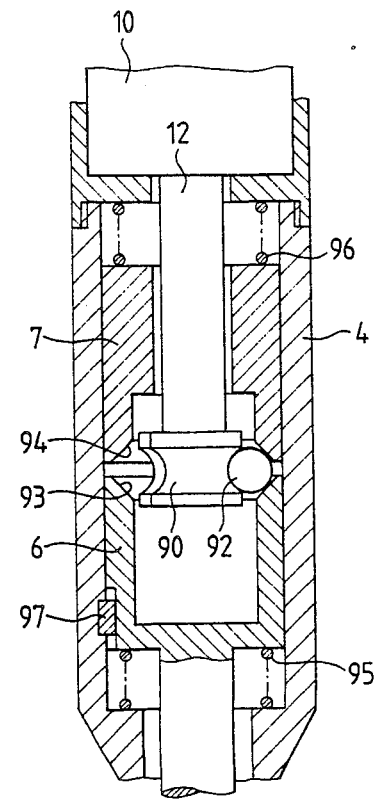
Figure 9:
Figure 10:
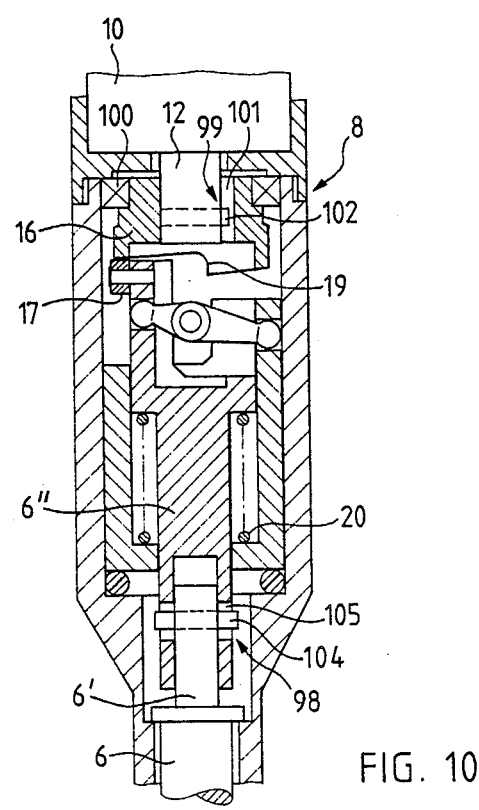
FIG. 10 is a longitudinal section of a scaler illustrating coupling means with a clearance.

In the embodiment according to FIG. 9 the end of striking rod 6 and striking body 7 are successively arranged and are provided on their facing faces with inclined planes 93, 94. A disk cam 90 is fixed to drive shaft 12 and its diameter constantly decreases and has a sudden transition 91 used for producing the sudden return movement of striking rod 6. A freely movable ball 92 is in operative connection with the disk cam 90 and is supported on the inclined planes 93, 94 of striking rod 6 or striking body 7. Through the action of in each case one working spring 95, 96 acting on striking rod 6 or striking body 7, ball 92 is held in clearance-free manner between the circumference of disk cam 90 and inclined planes 93, 94 of striking rod 6 or striking body 7.

If drive shaft 12 rotates, ball 92 is slowly forced outwards by disk cam 90, so that striking rod 6 and striking body 7 are driven apart counter to the tension of springs 95, 96, which leads to the slow movement of striking rod 6. At the sudden transition of disk cam 90, as a result of the tension of springs 95, 96 on inclined planes 93, 94, the ball moves suddenly on the smaller diameter of the disk cam, which leads to the sudden return movement of striking rod 6 with the scraper. A rotation of striking rod 6 is prevented by an ordinary key 97 inserted in the front casing part 4. In the case of the partly represented scaler of FIG. 10, it is shown that coupling means 99 are provided between drive shaft 12 and link disk 16, said coupling means having a clearance in the circumferential direction. To this end the link disk 16 is rotatably mounted, e.g. with an antifriction bearing 100 and has a slot 101, into which projects a bolt 102 inserted in drive shaft 12. The bolt diameter is smaller than the width of slot 101. Thus, on the transition of feeler roll 17 at the sudden transition 19, it is possible to displace the link disk 16 and consequently the sudden return movement takes place even more rapidly.

A further reinforcement of the striking action of striking rod 6 can be achieved by subdividing said rod into two partial rods 6', 6", which are held together with clearance by a coupling 98. Coupling means 98 comprise a pin 104 mounted in the striking rod portion 6' and a slot 105 in portion 6". If at the transition of feeler roll 17 at the sudden transition 19 the return movement is initiated, then initially only rod portion 6" moves and then the other rod portion 6", which carries the scraper, is suddenly moved backwards. As a result of the coupling means 98, 99 with a clearance, it is possible to reinforce the striking action of the scraper. It is obviously also possible to use said striking reinforcing coupling means in the other embodiments.

Figure 11:
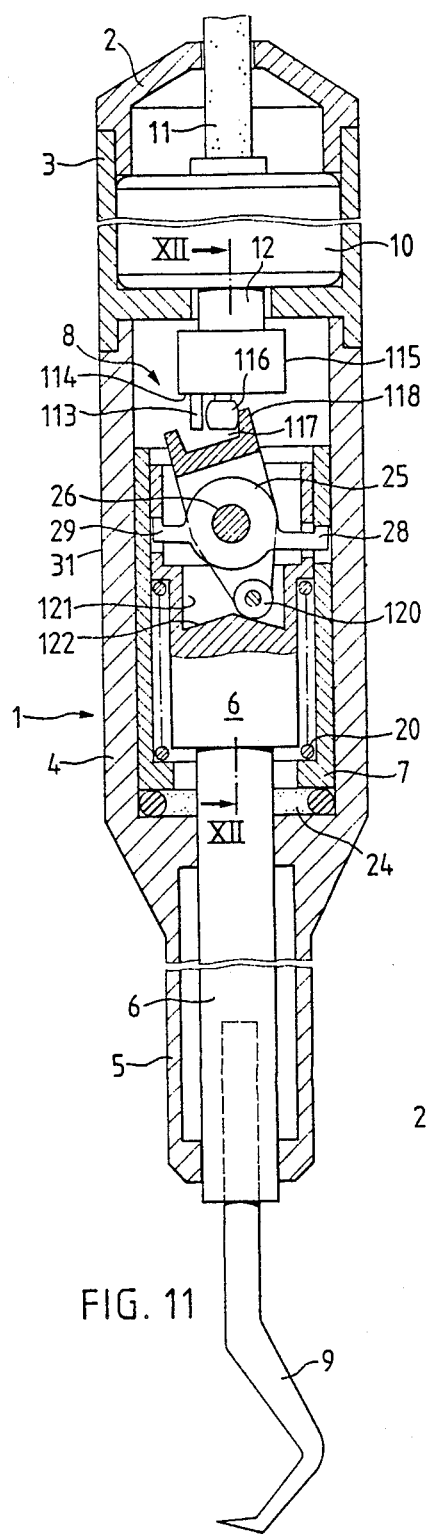
FIG. 11 is a longitudinal view through another scaler.
Figure 12:
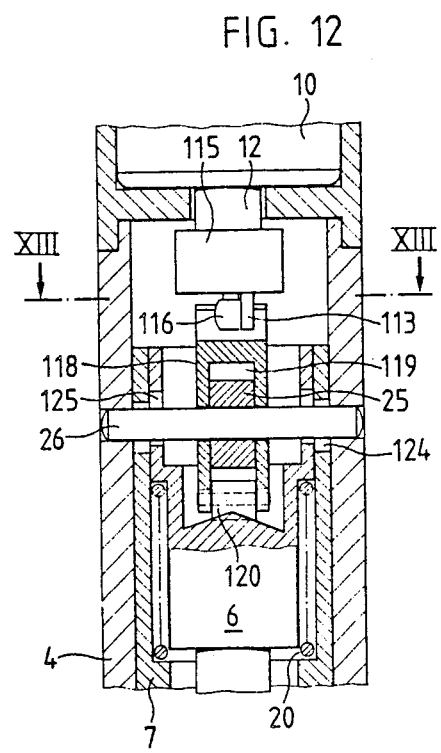
FIG. 12 is a cross section taken along line XII—XII in FIG. 11.

In the scaler embodiment according to FIGS. 11 to 12 the transition means 8 comprises a disk 115 driven by driven means 10, a cam follower 116 fixed to the face 114 of said disk, an eccentric pin 113 arranged alongside the cam follower 116 with a greater eccentric spacing than that of follower 116 and a tilting lever 118, the latter being pivotably mounted in the shaft 26 supported in the front casing part 4.

Figure 13:
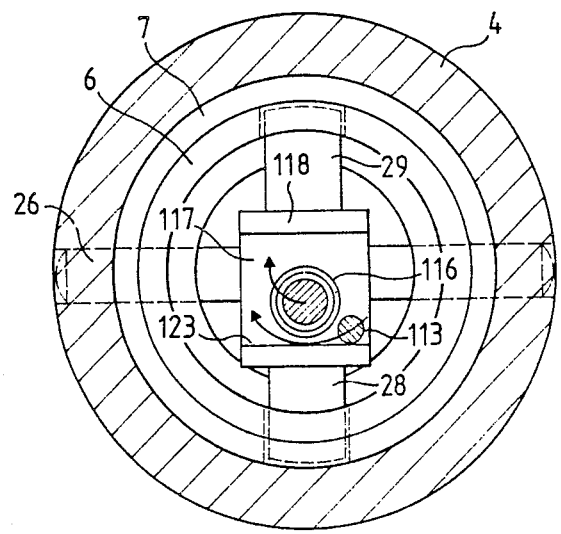
FIG. 13 is a view similar to that of FIG. 12 but drawn on a larger scale.

Cam follower 116 and eccentric pin 113 project into a depression of tilting lever 118, which is constructed as a slot 117. Thus, the depression is only bounded on two sides by walls on which can be supported cam follower 116 and eccentric pin 113. These conditions are shown on a larger scale in FIG. 13. In the represented position, cam follower 116 essentially performs no lifting movement, whilst the eccentric pin 113 gives an additional movement to tilting lever 118, because it lags with respect to the rotation direction of cam follower 116, preferably by approximately 20° to 45°. Thus, the feeler roll 120 of tilting lever 118 located on the opposite side of shaft 26 is moved at a higher speed over the highest protuberance of a conical surface 122 shaped in the bottom of a ball 121 in striking rod 6. As a result of this additional movement brought about by eccentric pin 113, it is ensured that the tilting lever 118, which moves on the conical surface 122 and forces striking rod 6 downwards against the tension of a spring 20, is instantaneously removed from the conical surface 122, so that the striking rod 6 is moved in the direction of drive move means 10 in a sudden or jerky manner as a result of the tension of spring 20.

FIG. 12 shows that the coupling lever 25 is located in a recess 119 of tilting lever 118 and on whose lower end is mounted feeler roll 120. Shaft 26 extends through slits 124, 125 in striking body 7 or striking rod 6, so that said body and said rod are prevented from rotating in handle 1. The use of the tilting lever 118 for producing the sudden or jerky return movement of the scaler has the advantage that the drive power is lower than when using a link disk. As a speed increase is obtained with the tilting lever 118, the power expended by the drive means 10 is correspondingly reduced.

The scaler described in the different embodiments can be easily handled by the operator. The speed or striking rate can be varied by correspondingly regulating the drive means 10. As required, sudden return movements can be achieved on scraper 9, it being possible to modify the travel of the return movement by using link disks 15 or disk cams 50, 90 with a different height of the sudden transition 90, 91. Compared with known scalers, it is possible to achieve a much higher output and this also does not fatigue the operator.

It is obvious that during the movements of scraper 9, the scaler can be moved manually over the tooth surface, only the scraping movements are being performed automatically.

While the fundamental novel features of the invention have been shown and described and pointed out, it will be understood that various substitutions and changes in the form of the details of the embodiments shown may be made by those skilled in the art without departing from the concepts of the invention a limited only by the scope of the claims which follow.

What is claimed is:

1. A process for treating periodontitis existing in the mouth of a patient having teeth with roots extending downwardly in the gums by using a scaler including a scraper with a cutting edge and a handle for the scraper, a dentist using the scraper to remove tartar, concretions and necrotic root element from a tooth by guiding the cutting edge along the tooth under the gums from the lowest point of the gum pocket and while exerting pressure on the root suddenly moving the cutting edge with a powerful jerk in scraping manner toward the chewing face of the tooth, the scaler being adapted for manual movement by the dentist and also having means which when actuated initiates and performs the jerk action without manual movement of the scraper by the dentist, said means including a striking rod and a striking body, said rod and said body moving in opposite directions, the rod producing the jerk action, the body producing a like counteraction, said process including the steps of manually moving the edge by manual operation of the dentist until the jerk action is desired and then automatically initiating and performing said action without manual movement of the scaler by the dentist.

2. A scaler for use in the treatment of periodontitis, said scaler comprising:
    an elongated striking rod having a bore in one end;
    a scraper having a projection with a cutting edge, the scraper having an opposite end disposed in said bore;
    an elongated handle, the scraper being disposed in the handle and being longitudinally movable back and forth along the direction of elongation within the handle, the bore containing end of the rod extending out of the handle;
    means in the handle for periodically initiating an action at which the rod is first moved rapidly outward with respect to the handle and almost immediately thereafter is moved rapidly inward to be returned to the original position in the handle, said means including a movable striking body coupled to the rod, said striking rod contained in part within said striking body, and an additional mechanism for causing the body to move in an opposite direction to the rod and produce a like counteraction when the action is periodically initiated.

3. The scaler of claim 2 wherein the means include a drive mechanism with a shaft which is continuously rotated about its axis and a camming mechanism disposed between the shaft and the rod to periodically initiate said action.

4. The scaler of claim 3 wherein the additional mechanism includes an additional shaft disposed in the handle and secured thereto, the additional shaft being isolated from the continuously rotating shaft, and a coupling lever pivotally mounted on the additional shaft and having first and second arms disposed on opposite sides of the additional shaft, one arm being coupled to the striking rod, the other arm being coupled to the striking body.

5. The scaler of claim 4 wherein the additional mechanism includes support rolls rotatably mounted on the additional shaft to prevent rotation of the striking rod and striking body.

6. The scaler of claim 5 wherein a cavity is disposed between the striking rod and striking body and a spring is disposed in the cavity.

7. The scaler of claim 3 wherein the striking body and striking rod are defined as striking elements and the camming mechanism includes a cam on the continuously rotating shaft and a follower secured to a selected one of the striking elements.

8. The scaler of claim 7 wherein the cam is selected from the group consisting of link disk and disk cam.

9. The scaler of claim 7 wherein the camming mechanism includes a disk cam with a sudden transition and a ball follower which cooperates with one of the striking elements.

10. The scaler of claim 3 wherein the camming mechanism includes a link disk on the continuously rotating shaft with a link disposed counter thereto, a flange connected to the striking body, a feeler ball disposed between the link and the flange, and a spring disposed between the flange and the rotating shaft.

11. The scaler of claim 3 wherein the camming mechanism includes a link support which rotates and has first and second link slots with sudden transitions, first and second feeler rolls, each roll cooperating with a corresponding slot, one roll being coupled to the striking rod, the other roll being coupled to the striking body.

12. The scaler of claim 3 wherein the striking rod has a conical surface and the camming mechanism includes a cam connected to the continuously rotating shaft and a cam follower cooperating with a feeler on the conical surface.

13. The scaler of claim 12 wherein the follower is provided with an eccentric pin.

* * * * *